United States Patent
Bachmann et al.

(10) Patent No.: US 6,860,738 B2
(45) Date of Patent: Mar. 1, 2005

(54) HYGIENE INSTRUMENT FOR CLEANING AND POLISHING THE SURFACE OF THE TEETH AND THE COMPOSITE MATERIALS OF DENTAL FILLINGS

(76) Inventors: Marc William Bachmann, 20 rue Biron, 34190 Ganges (FR); Sonia Bachmann, 20 rue Biron, 34190 Ganges (FR)

( * ) Notice: Subject to any disclaimer, the term of this patent is extended or adjusted under 35 U.S.C. 154(b) by 300 days.

(21) Appl. No.: 10/098,961

(22) Filed: Mar. 15, 2002

(65) Prior Publication Data

US 2002/0127513 A1 Sep. 12, 2002

Related U.S. Application Data

(63) Continuation-in-part of application No. 09/761,200, filed on Jan. 16, 2001, now Pat. No. 6,386,874, which is a continuation-in-part of application No. 09/561,803, filed on May 1, 2000, now abandoned.

(30) Foreign Application Priority Data

Nov. 26, 1999 (EP) .......................................... 999440327

(51) Int. Cl.[7] ................................................ A61C 3/06
(52) U.S. Cl. ...................................................... 433/142
(58) Field of Search ................................ 433/142, 141, 433/146, 147, 125, 166; 51/308, 298; 451/41

(56) References Cited

U.S. PATENT DOCUMENTS

| | | | |
|---|---|---|---|
| 1,813,675 A | 7/1931 | Moore | 433/142 |
| 2,122,920 A | 7/1938 | Russell | 433/142 |
| 2,474,684 A | 6/1949 | McCaughey | 433/142 |
| 2,937,446 A | 5/1960 | Weisenfeld | 433/142 |
| 3,698,388 A | 10/1972 | Muhler | |
| 3,775,848 A | 12/1973 | Barnett | |
| 4,462,136 A | 7/1984 | Nakao et al. | |
| 4,946,389 A | 8/1990 | Weissenburger | 433/142 |
| 5,114,438 A | 5/1992 | Leatherman et al. | 51/296 |
| 5,118,291 A | 6/1992 | Varaine | 433/142 |
| 5,273,559 A | * 12/1993 | Hammar et al. | 51/298 |
| 5,290,170 A | 3/1994 | Weissenfluh et al. | 433/142 |
| 5,697,390 A | 12/1997 | Garrison et al. | 132/321 |
| 5,797,748 A | 8/1998 | Reynaud et al. | 433/224 |

FOREIGN PATENT DOCUMENTS

| | | |
|---|---|---|
| EP | 0 425 357 A2 | 5/1991 |
| EP | 11192246 | 7/1999 |

* cited by examiner

*Primary Examiner*—Melba Bumgarner
(74) *Attorney, Agent, or Firm*—Young & Basile, P.C.

(57) ABSTRACT

Hygiene instrument for removing stains, cleaning and polishing the surface of the teeth and the composite materials of dental fillings.

The structure of the hygiene instrument is made up of fibers and optionally a load of particles embedded in a resinous matrix giving the working surface of the hygiene instrument a continuous abrasive power.

16 Claims, 2 Drawing Sheets

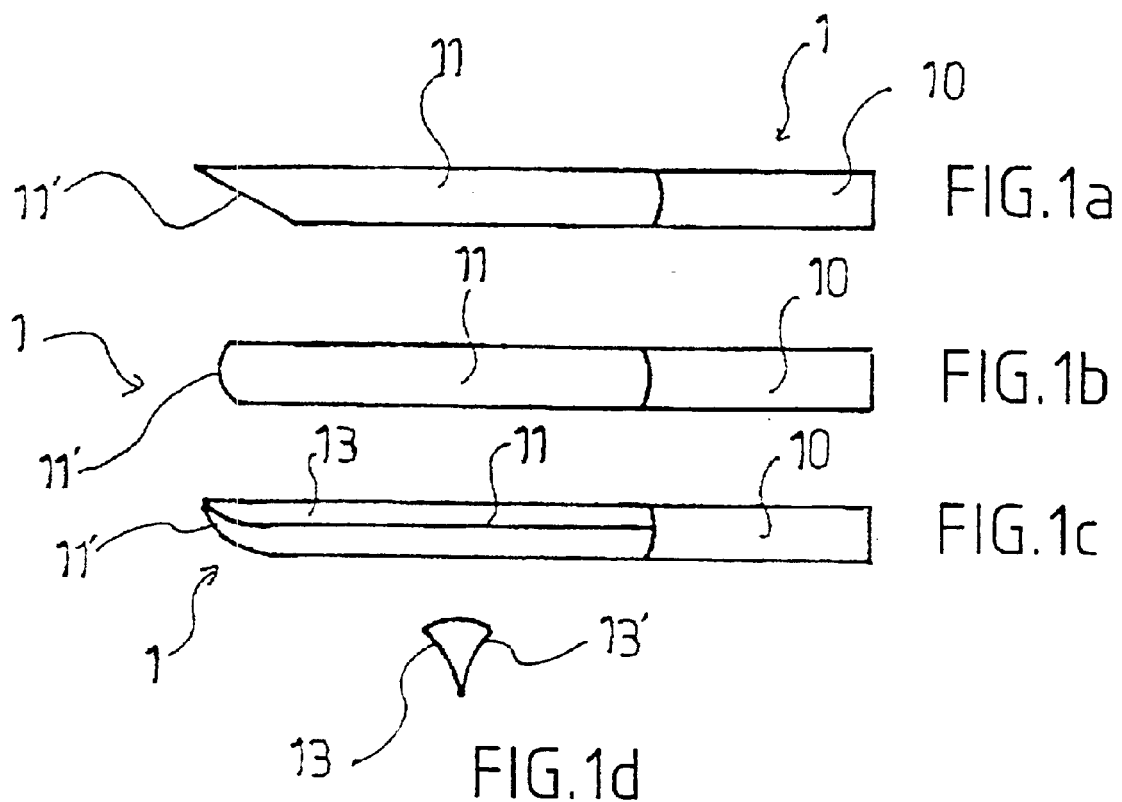
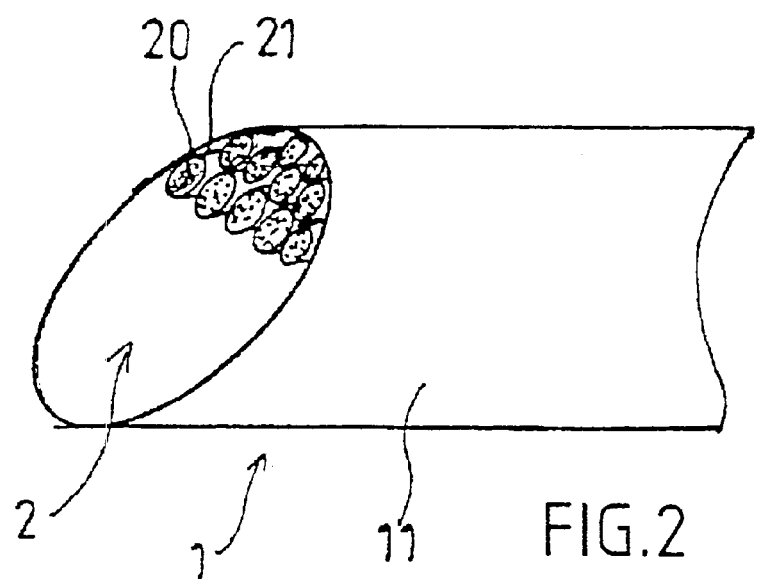

HYGIENE INSTRUMENT FOR CLEANING AND POLISHING THE SURFACE OF THE TEETH AND THE COMPOSITE MATERIALS OF DENTAL FILLINGS

This application is a Continuation-In-Part Ser. No. 09/761,200 filed Jan. 16, 2001, now U.S. Pat. No. 6,386,874 which is a Continuation-in-Part of Ser. No. 09/561,803 filed on May 1, 2000, now abandoned.

BACKGROUND OF THE INVENTION

The subject of this invention is an hygiene instrument, also called hereinafter polisher, for removing stains, cleaning and polishing the surface of the teeth and/or composite materials of dental fillings, the instrument or polisher being designed to be used by private individuals i.e., for home care as well as by practitioners of dental art.

One knows that correct maintenance of the teeth consists of daily elimination of dental plaque and food debris from the surface of the teeth and from the spaces between the teeth by a careful brushing, followed by the use of instruments used only once, such as toothpicks made of wood, plastic, or bird feathers; single tufted brushes; bottle brushes or dental floss.

However these instruments are not satisfactory.

The sticks, commonly called toothpicks, are made of wood or bird feathers and are not hygienic, they break easily, and they are traumatic to the gums; if made of plastic they are simultaneously too thick and too flexible and don't easily pass between the teeth.

Dental floss, made of silk or nylon materials, is efficient but has problems in crossing the point of contact of the teeth if these latter are too close from each other, and it shreds and remains stuck between the teeth, provoking immediate discomfort. The small brushes and the bottle brushes cannot be used when the spaces between the teeth are narrow, and their high cost is an obstacle to their regular use.

Dental professionals, dentists and hygienists must eliminate deposits, stains, and discolorations of the tooth surface and have, for the cleaning and polishing of the teeth and fillings made of composite materials, a vast array of instruments and devices, such as rotating brushes, instruments to remove tartar, ultrasonic instruments, air-polishers, or also abrasive strips or discs However, these instruments present the following drawbacks:

The rotating brushes, used with a cleaning powder, possess a very significant abrasive power that leads to excessive abrasion of the raised tooth surfaces. Furthermore, they cannot reach the interdental spaces to remove stains and deposits.

The instruments made of stainless steel that remove tartar only act at their points of contact with the tooth and are time and attention demanding, which leads to an elevated cost for a well done job.

Ultrasonic instruments have an end that is too large to go into small fractures and most of the time they are painful so that an anesthetic injection in the gum of the patient is rendered necessary.

Air polishers, which work like a micro-sandblaster by projecting a powder at a supersonic speed, unpolish the enamel, and consequently require a careful repolishing of the teeth with another otherwise adapted powder because in the absence of such a repolishing the surface of the teeth very quickly retarnishes. They are also rather painful in contact with gums.

Abrasive strips, made of fabric or plastic covered with an abrasive glue, introduced between the teeth and moved in a backwards and forwards movement are supposed to polish the proximal sides of the teeth, which requires the practician to hold the bands between the two fingers at each end in the oral cavity: this uncomfortable position does not allow one to correctly guide the strip to make it to conform to the shape of the proximal surface of the tooth. In addition, during this movement, if this extremely fine strip comes into contact with the gums, it can cut them like a razor and furthermore the strip loses its abrasive coat very quickly, which causes it to unglue itself while crossing over the contact point of the teeth if the teeth are sharp and/or very close from each other.

The abrasive disks, mounted on rotating instruments, are disks of a small diameter made of a plastic material covered with an abrasive material which can cut the gums and cannot penetrate the space between the teeth.

Finally, in a dental office, the difficulty, during the finishing and polishing of fillings made of a composite material, rests in the creation of a composite-tooth seal without excess while being perfectly polished. There still is a problem of access and of instrumentation more or less imperfectly adapted and not giving total satisfaction.

SUMMARY OF THE INVENTION

The goal of this invention is to remedy the drawbacks of existing instruments by proposing an instrument or polisher, with a low cost, which allows the cleaning and polishing of dental surfaces and which can be used by professionals without any pain or discomfort for the patient as well as private individuals.

The instrument or polisher for cleaning the surface of the teeth is created in the shape of a rod, which, in turn, can be shaped as a bur, and is characterized essentially by the structure of the rod which comprises fibers and optionally a load of particles embedded in a resinous matrix, the structure giving the working surface of the rod a continuous abrasive power effect and the rod being rigid.

DETAILED DESCRIPTION OF THE INVENTION

In a first embodiment of this invention, the rod is made only of abrasive fibers embedded in a resinous matrix and is rigid. The abrasive fibers give a scratching action, which removes stains.

In a second embodiment of this invention, the rod is made of abrasive fibers and a load of abrasive particles which are included in the resin matrix and is rigid, and the abrasive function created by the fibers or by the particles can be the same or different according to the choice of fibers and particles.

In a third embodiment of this invention, the structure of the rod is created from abrasive fibers and non-abrasive particles embedded in a resinous matrix, these unabrasive particles being able to smooth the abrasive power of the fiber and permitting to obtain a desired viscosity of the resin.

The structure of the rod can contain, in addition, a nucleus, made of a metal, a resin or a composite material, of a same or different type from the material forming the rod, and of the same or a different color.

The particles of the load allow, depending on their type, their shapes, their dimensions, and/or their quantity, to make varying the abrasive effect of the instrument, these particles, having preferably a hardness between 3 and 10 on the MOHS scale and a size between 2 and 25 microns.

The particles can be of the same size or have different sizes in order to diminish the interstitial spaces between adjacent particles and in order to promote regularity of the abrasive effect.

The load of these particles can vary from 5 to 30 weight % of the total weight of the resin plus the load of the particles.

The particles of the load incorporated into the resin during the fabrication process, of the instrument or polisher i.e. by extrusion, coextrusion, or by compression molding, transfer-compression, injection or pultrusion, allows one to obtain the researched viscosity to promote the sliding of the resin during the polymerization in the dies or in the molds. According to the method of production of the invention's instrument or polisher to be obtained, the particles of the load can be made:

on the one hand, of materials with an abrasive power, such as calcium carbonate, calcined clay, silica, glass or ceramic microspheres, aluminum oxide, such as alumina or even corundum, cerium oxide, tin oxide and mixtures or analogs thereof, on the other hand, of a material which does not possess an abrasive power but has a function of softening the abrasive effect procured by the fibers such as China clay or hydrated kaolin, talc, and a polytetrafluoroethylene (P.T.F.E.) sold under the trademark Teflon® powder, or of a mixture of the two preceding material types.

According to the invention, the fibers can be continuous or not, parallel or not, or assembled, for example, in the shape of coils, braids, or links.

When hardened, the resinous matrix gives rigidity to the polisher of the invention.

Still according to the invention, the proportion of the volume of fibers will be preferably from 45 to 65 volume % of the total volume of the fibers plus the resinous matrix, the resinous matrix optionally containing the load of particles, and the fibers can be glass fibers and notably AR glass fibers i.e. a glass enriched with zirconium oxide. Such volume proportions approximately correspond to weight percents varying from 45 to 55% of the total weight of the fibers plus the resinous matrix. The most preferably the fibers are chosen in the group constituted by fibers made of a glass which is enriched with zirconium oxide, fibers made of quartz or fibers made of pure silica. They can also be carbon fibers, or synthetic fibers, preferably aramide fibers such as Kevlar®. In all these alternatives, the fibers will have a diameter of between 2 and 25 microns, preferably of between 14 and 25 microns and most preferably of 20 microns.

In the first preferred embodiment of the invention, the fibers are fibers made of a glass which is enriched with zirconium oxide. These fibers give the instrument or polisher a very good resistance to acidic and/or alkaline agents and make the instrument detectable by electromagnetic radiation and, notably by X-rays, i.e. by a mere and common medical radiography.

In the second preferred embodiment of the invention, the fibers are made of quartz or pure silica. These fibers have the advantage, like fibers made of a glass which is enriched with zirconium oxide not to disintegrate in tiny fibrils, which disseminate in the mouth when the polisher of the invention is used, and to be resistant to alkaline or acid agents contrary to fibers of common glass.

In a third preferred embodiment, the polisher of the invention is made of fibers of quartz, pure silica or glass enriched with zirconium oxide and of a load of non abrasive particles, such as China clay, hydrated kaolites, talc or a polytetrafluoroethylene (P.T.F.E.) sold under the trademark Teflon® powder, embedded in a resin matrix.

In a fourth preferred embodiment of the invention, the fibers are fibers made of aramide, such as Kevlar® or Twaron®. These fibers enable to obtain a working surface, i.e a polishing surface, of the instrument or polisher of the invention, with a felt texture. In this latter case, the aramide fibers do not have any polishing function but they have the function to give the polishing surface of the polisher of the invention a felt texture and also they act as a rigid skeleton in the polisher of the invention. Consequently, in this embodiment, it is necessary to add abrasive powders either in the resin matrix of the polisher of the invention or onto its polishing surface. Such preferred abrasive polishing powders are powders of inorganic materials such as tin oxide or cerium oxide or alumina and mixtures of analogs thereof.

The resinous matrix will be made of thermohardening polymer resins or thermoplastic polymer resins and, preferably, of epoxy or polyester or polyether ketone (PEEK) resins and gives rigidity to the polisher of the invention.

The instrument or polisher of the invention can furthermore comprise surface treating agents, such as titanates, zirconates, or preferably silanes, in order to increase the adhesion of the particles to the resin.

The structure of the instrument or polisher according to the invention thus enables one to give the polisher the fineness required to access the tightest spaces between the teeth, without risk of fracture and without danger for the teeth or the periodontal area, as well as all the desired shapes to conform to the dental surfaces as closely as possible.

In addition, the structure of the instrument or polisher with abrasives fibers according to the invention gives it a permanent abrasive power, because the abrasive agents are entirely a part of its structure and, as one goes along using this instrument, the working surface of the instrument or polisher always includes new sections of fibers and/or particles which insure its abrasive function.

Finally, its structure enables it to be cleaned, decontaminated, or sterilized and renders it an instrument or polisher perfectly adapted to the hygienic and biocompatibility requirements for a use in the oral cavity.

The instrument or polisher according to this invention thus offers to private individuals a means of hygiene and maintenance of their teeth which is efficient, easy to use, without danger, and economical, also enabling them to eliminate the stains and undesirable discoloration, even in places difficult to access, and such a polisher had no equivalent until the invention.

As already disclosed above, the polisher of the invention can be used as well by private individuals as by professionals.

When to be used by private individuals, the polisher of invention must have a shape that permits it to be taken by hand. Thus, preferably the polisher of the invention is constituted of a rod comprising fibers and optionally a load of particles, both the fibers and the particles being embedded in a resinous matrix, at least one end of which is beveled.

In one embodiment, the rod has only one beveled end, which is the end to be applied to the teeth, i.e. the working end. The other end of the rod is used to handle the polisher of the invention.

In another embodiment, the rod still has one beveled and i.e. the working end and, at the other end, a handle made of different material.

However, the polisher of the invention can also have each of its end beveled, both of them being working ends. In this case, preferably one end has a thin and pointed shape in order to penetrate in the interdental spaces and the other end has a rectangular beveled cross section in order to permit to rub the front and rear surfaces of the teeth. Otherwise stated, the polisher of the invention has the shape of the tooth sticks made of wood that presently exists.

Professionals in their practice can also use this hand polisher.

However, for those professionals, the polisher of the invention can be shaped as burs made from the inventions rod. The burs work by being fixed by a latch or friction grip attachment into a rotating dental hand piece or contra-angle that every dentist owns. Consequently, no further expenses are incurred such expenses incurred for buying special devices.

These burs can be used with success:

to remove stains and to clean teeth, to polish the enamel after ultrasonic scaling. Indeed to remove calculus, the dentists use hand scalers and ultrasonic scaling and, when this procedure is achieved, tiny particles remain in the mouth and on the teeth and give to the patient the feeling of rough surfaces. The use of the rotating burs made according to the invention eliminates these relieves and give and gives a smooth and comfortable feeling, to eliminate soft tartar deposits from the buccal surface of the teeth which are difficult to be reached, to grind composite fillings, in particular the excess of composite in the interdental spaces where no instrument is able to do a quick and nice job. Indeed, diamond burs used to do it are too much abrasive, they grind the enamel, the composite and the dentin, resulting in grooves instead of a smooth surfaces.

However the burs of the invention can also be used for root surfacing. Indeed, in periodontal therapy, to remove calculus the dentist proceeds under gingival, either in a blind manner or with a gingival flap surgery, first with hand scalers and ultrasonic scalers. To be successful in this therapy, it is necessary to obtain completely smoothen root surfaces; to do this particular work, the burs of the invention are particularly suitable because they polish the enamel without grinding it an they gently sand the dentin of the root, giving clean and smooth surfaces.

These operations are done by rotation of the burs at low and medium speeds or from 1,000 to 5,000 RPM under a flow of water into the gingival sulcus, to wipe away all grinding dusts.

The instrument or polisher of this invention enables dental professionals to gain a considerable time and efficiency and gives their patients, more comfort, and better results, without any loss of their dental integrity, and at a lower cost and above all without any pain or discomfort.

Another advantage of the instrument or polisher of the invention is its low cost. Indeed, they are shaped, from the rod of the invention, in one single operation. Then, they are ready to be used, contrarily to a diamond bur that needs to be shaped as a preform from a steel rod, then glued and covered with diamond powder which is nickel-electroplated to bond it, and then laser engraved.

Furthermore dental devices of the prior art, which have a significant cost, must be cleaned and sterilized prior to be reused. In case of any failure in the sterilization chain there is a major danger to make a cross contamination between patients.

For this reason more and more medical materials are for unique use i.e. disposable.

The burs according to the invention have a low price so that they can be sold s disposable burs to be used only one time and thrown away: this advantage and the efficiency at the burs of the invention give the dental practice and public health an effective low cost and safe instruments which are not existing today.

The burs of the invention can also be advantageously used to enlarge the gingival sulcus before taking impressions at chair side. Such an enlargement conducted with the burs of the invention is advantageous because it produces a soft peeling of the gingival, contrarily to the enlargement conducted with the presently used diamond burs, while still permitting a good healing.

BRIEF DESCRIPTION OF THE DRAWINGS

The advantages and features of the present invention will become clearer in the following description, which is made in relation to the attached drawings representing a non-limiting embodiment.

FIG. 1a is a profile view of a tooth-cleaning instrument or polisher according to the invention following a particular form;

FIG. 1b is a profile view of a tooth-cleaning instrument or polisher according to the invention following another form;

FIG. 1c is a profile view of a tooth-cleaning instrument or polisher according to the invention according to another form;

FIG. 1d is an end view of the instrument or polisher represented in FIG. 1c;

FIG. 2 represents a partial, transversely cut view of a tooth-cleaning instrument or polisher according to the invention in a preferred embodiment of its internal structure;

DESCRIPTION OF THE PREFERRED EMBODIMENTS

Figure 3A:
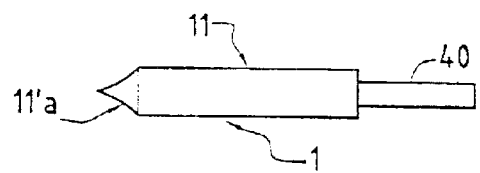
FIG. 3a is a profile view of a polisher for professionals following a particular shape.
Figure 3B:
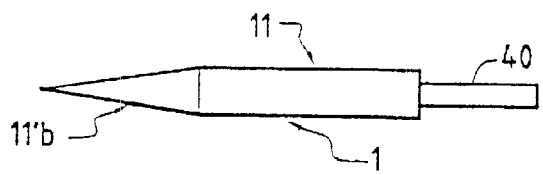
FIG. 3b is a profile view of a polisher for professionals following a second particular shape.
Figure 3C:
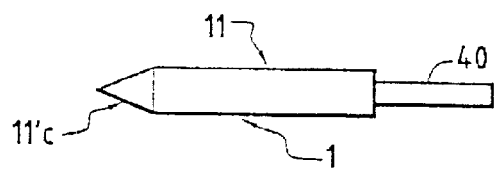
FIG. 3c is a profile view of a polisher for professionals following a third particular shape.

If one refers to FIGS. 1a, 1b, and 1c, one can see that a tooth-cleaning instrument or polisher according to the present invention presents itself in the shape of a rod 1 consisting of a handle 10 to hold on to and a part 11 comprising a working end 11' enabling one to polish the surface of teeth. The handle 10 and part 11 will preferably be made of only one piece i.e. of the same material as is the case in the figures, or the handle 10 will be an added part made of a different or same material as the part 11.

The part 11 has a cylindrical shape and its working end 11' is beveled obliquely (FIG. 1a), or in a manner more or less rounded (FIGS. 1b and 1c), or is straight. One can also see in FIGS. 1c and 1d that part 11 can also be beveled longitudinally in such a manner to form two adjacent sides 13, 13', forming a certain angle there between and slightly curved.

The working end 11' can have many various shapes, as well in order to penetrate different spaces between teeth, especially very small spaces, as in order to be able to clean and polish the teeth by moving the rod in a back and forth, an up and down, movement in contact with the surfaces to be cleaned.

The polishing of the teeth is made possible thanks to the particular structure 2 of the rod 11 which gives it, during the entire polishing operation, an abrasive power which continuously renews itself. The structure 2 is made up of, as one can see on FIG. 2, abrasive fibers 20, each forming a file, embedded in a resinous matrix 21 preferably made on the basis of an epoxy resin.

In the first particularly preferred embodiment, the instrument or polisher of the invention is constituted of fibers 20 made of glass enriched with zirconia $ZrO_2$, these fibers 20 bing embedded in a resin matrix. The fibers 20 made of a glass which is enriched with zirconium oxide are fibers manufactured from a glass which has itself been manufactured by melting raw materials powders among which zirconium oxide or a precursor of zirconium oxide. In this glass, zirconium oxide replaces and substitutes to a part of the other usual constituents of a glass as well before as after the melting of the constituents of the glass i.e. the manufacture of the glass. For use in the invention the glass from which the fibers 20 are manufactured preferably contains between 15 and 20% by weight of zirconium oxide as compared to the total weight of the constituents of the glass and the most preferably between 16,8 and 17,1% by weight of zirconium oxide as compared to the total weight of the constituents of the glass. From this glass, glass fibers are spun and then embedded within a resin matrix. Then one gives the desired shape to the instrument or polisher of the invention and, as already described, the working end 11' is beveled either obliquely or in a more or less rounded fashion or longitudinally in order to form two adjacent faces 13, 13', which make a certain angle between them and slightly curved.

This polisher containing fibers of a glass enriched with zirconium oxide possesses numerous advantages.

First of all, the fibers 20 made of a glass enriched with zirconium oxide are resistant to acid and/or alkaline agents and consequently render the polisher of the invention resistant to acid and/or alkaline agents. This is very interesting because the mouth is a medium, which can alternatively be acid or alkaline.

That is to say that the fibers 20 made of a glass enriched with zirconium oxide, contrarily to classic glass fibers made of glass non enriched with zirconium oxide, are not attached by acid or alkaline agents present in the mouth, during their use in the mouth, and consequently do not lead to the formation of residues which could be noxious.

Furthermore, the fibers 20 made of a glass enriched with zirconium oxide are radiopaque to electromagnetic radiations and thus render the instrument or polisher of the invention detectable by X-rays, enabling to locate it in case of accidental ingestion.

But more importantly, contrarily to the classic glass fibers, which disintegrate in tiny fibrils when used as a polisher, these fibrils overunning the mouth, the fibers made of a glass which is enriched with zirconium oxide do not produce such fibrils.

Indeed, a dental instrument or polisher made from fibers of classic glass, i.e. a glass non enriched with zirconium oxide, when used as a polisher, forms small fibrils which are irritating and even dangerous for the mucosa and soft parts of the user. These fibrils are even more dangerous if they are swallowed. The user, when using a polisher constituted of such fibers made of a classic glass, such as E glass, has the mouth filled with such fibrils, rendering such a polisher particularly dangerous and unpleasant to use. In contract, the polisher of the invention made from fibers of a glass enriched with zirconium oxide does not have such drawbacks.

In a second particularly preferred embodiment of the invention, the instrument or polisher of the invention is constituted of quartz or pure silica fibers embedded in a resinous matrix.

Indeed such a polisher possesses the same advantages as the polisher constituted of fibers made of a glass enriched of zirconium oxide according to the first preferred embodiment of the invention, except that they do not render the polisher or instrument radiopaque.

According to a particularly third preferred embodiment of the invention, the polisher of the invention is constituted of fibers made of a material chosen from the group constituted of a glass enriched with zirconium oxide, pure silica fibers and quartz fibers or a mix of them and of a load of particles of a material chosen from the group consisting of China clay, hydrated kaolin, talc and a polytetrafluoroethylene (P.T.F.E.) sold under the trademark Teflon® powder, the fibers and particles being embedded in a resinous matrix. Indeed, by incorporating such a load of particles of such a material, which does not possess an abrasive powder of the fibers, is soften and one is allowed to obtain the researched viscosity of the resin.

The softening of the abrasive powder of the fibers presents the advantage of obtaining a good cleaning and whitening of the teeth without excess noxious abrasive action when this polisher is used.

The viscosity of the resin that is researched is the one that promotes the sliding of the resin in the dies or in the molds in which the polisher of the invention is manufactured.

Preferably, the particles constitute from 5 to 30 weight percent of the total weight of the resin and particles.

This means that one adds from 5 to 30 weight parts of particles into 70 weight parts of resin.

The preferred load of particles is constituted by China clay. In this case, preferably the load of China particles constitutes from 5 to 10 weight percent of the total weight of the resin particles.

In a fourth particularly preferred embodiment of the invention, the instrument or polisher of the invention is constituted of aramide fibers, such as Kevlar® fibers, embedded in a resin matrix. The aramide fibers are particularly advantageous because when they are put at the desired shape, for example by machining, they produce filaments that do not completely take off from the machined part. This behavior is generally considered as a drawback of these fibers but, in the case of the polisher of the invention, this behavior is an advantage.

Indeed, during the manufacture of the beveled working end 11' of the polisher of the invention, this behavior enables to create a surface of the working end 11' which has a felted texture, and this is particularly advantageous in the case of a polisher.

However, the aramide fibers do not have any polishing function. Here, they have the function to create the rigid skeleton of the polisher of the invention and also to create a surface of the working end 11' having a felted texture. Then it is necessary to add abrasive powders in the resin matrix of the polisher of the invention. However the abrasive powders may also be added onto the surface of the working end 11', before each use. Preferred abrasive powders that can be used for this aim are powders of tin oxide or cerium oxide or alumina and a mixture thereof.

Whereas the polisher according to the first preferred embodiment of the invention in which the fibers 20 are fibers made of a glass which is enriched with zirconium oxide, or of pure silica or quartz, is more particularly designed for a domestic use, by the private individual, the polisher of the invention according to the fourth preferred embodiment in which the fibers 20 are aramide fibers and in which the resin matrix furthermore contains abrasive agents such as tin oxide, cerium oxide or alumina, is more particularly designed for a use by a professional. Indeed, it can be used not only by hand, but also fixed to an apparatus capable to put it in rotation or vibration.

However, the polisher according to the first, second and third embodiments of the invention are also usable by a professional in the shape of burs.

When the polisher of all the embodiments of the invention is to be used by professionals, it is particularly advantageous that the polisher be specifically designated under a shape that render it usable with the rotating instrument, usually used by these professionals.

Indeed, presently diamond burs are too abrasive and indifferently grind down as well the enamel as the dentine of the teeth that creates notches and grooves in the sound enamel of the teeth, impairing the protective function of enamel against dental decays.

Furthermore, the important abrasive power of the diamond burs erases the differences of relief existing between the enamel and the dentine insuring deflection of food and keeping them away from the gums around the tooth, which is very important for the prophylaxis of parodontopathies.

Moreover, the polisher of the invention does not create any pains or discomfort for the patient, contrarily to the polisher presently used.

For this aim, the polisher of the invention can be shaped to fit contra-angles and hand pieces like the burs used by the professionals when rotating movements on the teeth are wanted.

Thus, the polisher of the invention can be shaped in order to fit contra-angles or hand pieces presently used by the professionals when an alternative back and forth or up and down movement or a combination a back and forth and up and down movements on teeth are wanted.

These shapes are well known from the man skilled in the art and exist at the present time for diamond burs.

Figure 3D:
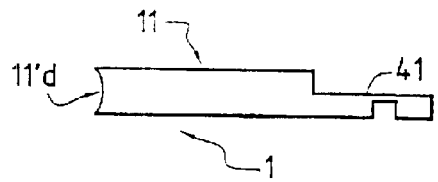
FIG. 3d is a profile view of a polisher for professionals following a fourth particular shape.
Figure 3E:
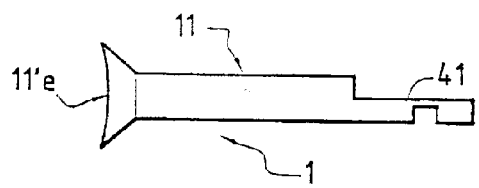
FIG. 3e is a profile view of a polisher for professionals following a fifth particular shape.

For example, the polisher of the invention can have the shape of a rod 11 of a diameter of 2,35 mm and a length between 15 and 30 mm having a working end an active portion (the working end 11') and at the other hand a shape 40, 41 designed for fitting in the presently existing dental tools support of burs such as contra-angles or hand pieces used by the professionals such as presented in FIG. 3de.

The active portion or working end 11', the polisher may have any shapes such as the shape of a shell, a pear or straight or concave cones with more or less sharp angles as represented in FIG. 3a.

Such shapes are particularly appropriate for cleaning and polishing the interdental spaces and curve parts of the teeth.

However, the working end 11' can also be flat or have an inversed cone shape, as represented in FIG. 3d.e. Such shapes are particularly appropriate for cleaning and polishing wide tooth surfaces.

Figure 3F:
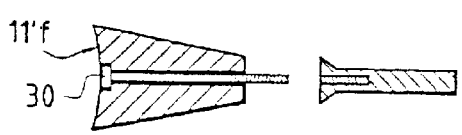
FIG. 3f is a profile view of a working end of a polisher for professionals following a sixth particular shape.

The working end 11' can also have the shape of a unitary inversed cone the center of which can be pierced in order to enable it to be fixed through a screw 30 into the head of the contra-angle which issues its rotation, as represented in FIG. 3f.

Figure 3G:
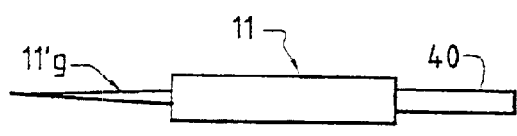
FIG. 3g is a view from above of a polisher for professionals following a seventh particular shape.
Figure 3H:
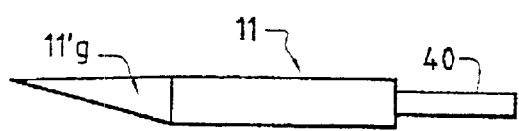
FIG. 3h is a profile view of the polisher for professionals following the eight particular shape.
Figure 3I:
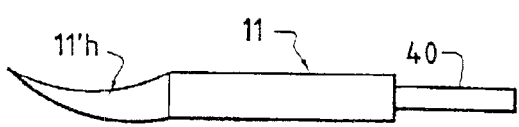
FIG. 3i is a profile view of the polisher for professionals following a ninth particular shape.

Finally, the working end 11' may have the shape represented in FIG. 3g.i. i.e. the shape of a straight or concave knife blade.

Such shapes are particularly appropriate for cleaning and polishing not only the interdental spaces but particularly for removing form the use interdental spaces the filling composite cement in excess without damaging the dental enamel.

In any cases, the proportion of the fibers 20 is advantageously between 45 and 65% by volume of the total volume of the fibers plus the resinous matrix plus the load of particles, when such a load is present, in order to obtain a good polishing power, and the fibers 20 preferably have a diameter of between 2 and 25 microns, preferably of between 14 and 25 microns, and most preferably of 20 microns.

The fibers 20 are preferably continuous fibers embedded in a resin matrix which do not produce particles that can disseminate into the oral cavity.

Another common advantage of the polishers according to the first and second preferred embodiments of the invention is that they are usable not only for polishing natural teeth but also for polishing composite materials which are used as dental filling material or as material for a dental prosthetic element.

In particular the polisher according to the first preferred embodiment of the invention is which the fibers 20 are fibers made of a glass which is enriched with zirconium oxide can be used for giving the shape to the composite material and for obtaining a smooth and appropriate surface of the dental composite material. However the dental composite material after such a polishing with such a polisher has a matte finish and therefore should be rendered bright by a finer polishing. This is advantageously obtained by using the polisher according to the second preferred embodiment of the invention, in which the fibers 20 are aramide fibers, this polisher being preferably placed on a device that enables to put the polisher of the invention in rotation or vibration. This finishing enables to attain a bright aspect that is very closed from, if not identical to, the natural dental enamel.

It is to be noted that when the polisher according to the first preferred embodiment of the invention in which the fibers 20 are fibers made of a glass that is enriched with zirconium oxide s used on natural tooth, it does not abrade the enamel so that the natural tooth keeps its bright aspect.

Thus, the instrument or polisher of this invention allows cleaning and polishing of the dental tissue, while respecting the tooth as well as cleaning and polishing parts made of a composite material for dental restoration, and because of its bio-compatible characteristics, is particularly adapted to the required conditions for the use in the oral cavity.

Finally, its abrasive power can be chosen and determined according to the needs by acting on the nature of each of these constituents, that is to say, the fibers and/or the particles embedded in the resin matrix.

The above is also true for the polisher according to the second and third embodiments of the invention.

In all the embodiment of the polisher of the invention, the abrasive action is given by the ends of fibers 20 and/or the load of particles appearing at the surface of the working end 11' of the fibers 20, this abrasive action consequently renewing itself as one goes along using the instrument or polisher of the invention.

As already stated, in all the embodiments of the invention, the polisher is rigid due to the hardened resinous matrix.

The polisher of the invention is most preferably manufactured by the pultrusion process that means that the fibers are essentially continuous fibers extending along the axial direction of the polisher. However, is this pultrusion process the fibers can also be twisted or winded or used in a form of a braid.

The finished pultruded product is a rod. This rod will be machined by known industrial process, like a grinding, to produce the polishers of the invention.

The section of the rod and of the polisher preferably is round but it can be produced and used in any geometric shape like square, triangle, oval, pentagon, hexagon, octagon, etc.

What is claimed is:

1. Hygiene instrument for cleaning, removing stains and polishing the surface of teeth and/or composite materials of dental fillings wherein the instrument has a shape of a rod and wherein a structure of the rod comprises fibers selected from the group consisting of fibers made of quartz and fibers made of pure silica, embedded in a resinous matrix giving a continous abrasive power to a working surface of the rod; and the structure of the rod furthermore comprises a load of particles selected from the group consisting of china clay, hydrated kaolin, talc and a polytetrafluoroethylene powder.

2. Hygiene instrument for cleaning, removing stains and polishing the surface of teeth and/or composite materials of dental fillings wherein the instrument has a shape of a rod and wherein a structure of the rod comprises fibers selected from the group consisting of fibers made of quartz and fibers made of pure silica, embedded in a resinous matrix giving a continuous abrasive power to a working surface of the rod, wherein the structure of the rod furthermore comprises a load of particles of china clay.

3. The instrument according to claim 1 wherein the resinous matrix is made of one of a thermohardening polymer matrix and a thermoplastic polymer matrix.

4. The instrument according to claim 1, wherein the fibers constitute between 45 and 65% by volume of the rod.

5. A The instrument according to claim 1 wherein the load of particles constitutes between 5 and 30% by weight of the rod.

6. The instrument according to claim 1 wherein the rod has a cylindrical shape of which one end is beveled.

7. The instrument according to claim 6 wherein the beveled end is longitudinally beveled in such a manner to form two adjacent sides making a specific angle there between.

8. The instrument according to claim 1 comprising a handle created in one piece with the rod, this handle being made from the same material as the rod.

9. The instrument according to claim 1 comprising a handle created in one piece with the rod, this handle being made of the material different from the rod.

10. The instrument according to claim 1 wherein the rod has two beveled ends, one end having a thin and pointed shape for penetrating into the interdentals spaces and the other end having a rectangular cross section and being beveled to rub the internal and external surfaces of the teeth.

11. Hygiene instrument for cleaning, removing stains and polishing the surface of teeth and/or composite materials of dental fillings wherein the instrument has a shape of a rod having two beveled ends, one end having a thin and pointed shape for penetrating into the interdental spaces and the other end having a rectangular cross section and being beveled to rub the internal and external surfaces of the teeth and wherein a structure of the rod comprises fibers made of a glass which is enriched with zirconium oxide embedded in a resinous matrix giving continuous abrasive power to a working surface of the rod, wherein the structure of the rod comprises a load of particles selected from the group consisting of china clay, hydrated kaolin, talc and a polytetrafluoroethylene powder.

12. The instrument according to claim 11 wherein the load of particles constitutes between 5 and 30% by weight of the rod.

13. Hygiene instrument, for use by professionals, for cleaning, removing stains and polishing the surface of teeth and/or composite materials of dental fillings wherein the instrument has a shape of a bur and wherein a structure of the bur comprises fibers selected from the group consisting of fibers made of a glass which is enriched with zirconium oxide, fibers made of quartz and fibers made of pure silica, embedded in a resinous matrix giving a continuous abrasive power to a working surface of the bur wherein the structure of the bur furthermore comprises a load of particles selected from the group consisting of china clay, hydrated kaolin, talc and a polytetrafluoroethylene powder.

14. The instrument according to claim 13 wherein the resin matrix is made of one of the thermohardening polymer matrix and thermoplastic polymer matrix.

15. The instrument according to claim 13, wherein the fibers constitute between 45 and 65% by volume of the rod.

16. Hygiene instrument for use by professionals, for cleaning, removing stains and polishing the surface of teeth and/or composite materials of dental fillings wherein the instrument has a shape of a bur and wherein a structure of the bur comprises fibers selected from the group consisting of fibers made of a glass which is enriched with zirconium oxide, fibers made of quartz and fibers made of pure silica, embedded in a resinous matrix giving a continuous abrasive power to a working surface of the bur, wherein the structure of the bur furthermore comprises a load of particles of china clay.

* * * * *